United States Patent [19]

Cheminal et al.

[11] Patent Number: 4,849,555
[45] Date of Patent: Jul. 18, 1989

[54] SYNTHESIS OF 1-CHLORO-1, 1-DIFLUOROETHANE

[75] Inventors: Bernard Cheminal, Brignais; André Lantz, Vernaison, both of France

[73] Assignee: Societe Atochem, Puteaux, France

[21] Appl. No.: 205,941

[22] Filed: Jun. 13, 1988

[30] Foreign Application Priority Data

Jul. 3, 1987 [FR] France ................................ 87 09495

[51] Int. Cl.$^4$ ....................... C07C 17/20; C07C 19/02
[52] U.S. Cl. .................................................... 570/165
[58] Field of Search .......................................... 570/165

[56] References Cited

U.S. PATENT DOCUMENTS 4,374,289  2/1983  Van Der Puy et al. ............ 570/165

FOREIGN PATENT DOCUMENTS 2659046  7/1977  Fed. Rep. of Germany .
684117  12/1952  United Kingdom ................ 570/165

Primary Examiner—J. E. Evans
Attorney, Agent, or Firm—Stevens, Davis, Miller & Mosher

[57] ABSTRACT

The invention relates to a process for the manufacture of 1-chloro-1,1-difluoroethane in the liquid phase by reacting hydrofluoric acid with 1,1,1-trichloroethane and/or 1,1-dichloro-1-fluoroethane.

The selectively is improved by using a perfluoroalkanesulphonic acid, in particular trifluoromethanesulphonic acid, as a catalyst.

12 Claims, No Drawings

SYNTHESIS OF 1-CHLORO-1, 1-DIFLUOROETHANE

FIELD OF THE INVENTION

The present invention relates to the manufacture of 1-chloro-1, 1-difluoroethane, $CF_2Cl-CH_3$, by the catalytic reaction of 1,1,1-trichloroethane, $CCl_3-CH_3$, with hydrofluoric acid, HF, in the liquid phase.

BACKGROUND OF THE INVENTION

1-Chloro-1, 1-difluoroethane is used particularly as an intermediate in the synthesis of 1,1-difluoroethylene, $CF_2=CH_2$ (itself a monomer of increasing importance for the industrial production of fluorinated polymers), but also as an aerosol propellant. It is generally prepared by reacting 1,1,1-trichloroethane with hydrofluoric acid in the liquid phase.

In a known process (German Patent No. 2,137,806), the reaction can be carried out without a catalyst provided the temperature is high (110° C.) and there is a large excess of hydrofluoric acid (molar ratio $HF/C_2H_3Cl_3$ between 15 and 30). This gives a substantial amount of 1,1,1-trifluoroethane as a by-product and results in a low productivity in terms of 1-chloro-1,1-difluoroethane. Furthermore, the entrainment of hydrofluoric acid by the hydrochloric acid formed in this chlorine ⟷ fluorine exchange reaction makes it necessary to use specially adapted equipment (under a sufficient pressure) to recover this expensive raw material. The patent mentioned above indicates that the use of $HSO_3F$ results in the formation of tars, probably due to the chemical instability of this catalyst (oxidation by $SO_3$).

Other known processes recommend the use of catalysts based on antimony or molybdenum derivatives. See, for example, German Patent No. 2,659,046 and Japanese publication Nos. 74-03965, 76-29404 and 76-39606.

The major disadvantage of antimony derivatives is the fact that they are rapidly deactivated by reduction to the lower oxidation state $Sb^{3+}$. The answer to this, which consists of continuous oxidation of the catalyst (with chlorine), contributes to the formation of heavy compounds (derived from chlorination of the $CH_3$ group of the 1,1,1-trichloroethane). Furthermore, the solubility of some catalytic species (for example $SbF_3$) in the reaction medium is so low that it usually causes physical separation of this species and renders the action of the chlorine ineffective. As a result, the chemical reaction is non-uniform, a large amount of catalyst is consumed. There is sustained corrosion due to the formation of superacidic compounds which are very aggressive towards the reactor material. Finally, the difficulty of suitably controlling the catalytic activity leads to the undesirable formation of a substantial amount of 1,1,1-trifluoroethane as a by-product.

With molybdenum derivatives, the formation of volatile species results in a loss of catalyst in the gas phase of the reactor.

The preceding references are incorporated by reference.

SUMMARY OF THE INVENTION

It has now been found that it is possible to overcome these disadvantages and carry out the reaction with a reasonable excess of hydrofluroic acid (molar ratio $HF/CH_3-CCl_3$ between 2 and 5) by using an acid catalyst which is soluble in the reaction medium and comprises a perfluoroalkanesulphonic acid $CF_3-(CF_2)_n-SO_3H$, where n can range from 0 to 7 and is preferably equal to zero (triflic acid, $CF_3-SO_3H$).

DETAILED DESCRIPTION OF THE INVENTION

The catalyst according to the invention is advantageously used in an amount of 1 to 10 mol per 100 mol of 1,1,1-trichloroethane and preferably in an amount of 3 to 5 mol per 100.

The process according to the invention can be carried out batchwise or continuously, at a temperature which ranges from 80° to 150° C. but is preferably around 100°–110° C.

The batch process is carried out in a closed reactor into which all the reactants are introduced at the start of the operation and in which the autogenous pressure increases up to a maximum value.

In the continuous process, the reactants are pumped into the reaction mixture containing the catalyst, with continuous recovery of the useful compounds (1-chloro-1,1-difluoroethane and hydrochloric acid) and condensation of the heavier compounds (catalyst, hydrofluoric acid, 1,1,1-trichloroethane, 1,1-dichloro-1-fluoroethane). The total pressure is maintained at a given value by means of an appropriate regulating device. The working pressure must be sufficient (equal to at least 15 bar and preferably between 15 and 20 bar) to enable the hydrochloric acid to be separated out by distillation and to keep the reactants in the liquid state.

The 1,1-dichloro- 1-fluoroethane formed is advantageously recycled for conversion to 1-chloro-1,1-difluoroethane.

EXAMPLES

The examples below, in which the percentages indicated are expressed in mol, illustrate the invention without implying a limitation.

EXAMPLE 1

3.2 g of triflic acid, 71 g of 1,1,1-trichloroethane and 23.3 g of hydrofluoric acid are introduced successively into an 800ml stainless steel autoclave (NS 22 S) fitted with a stirring system of the magnetic bar type.

With the stirrer running at about 700 rpm, the reaction mixture is heated to 100° C. by means of a heat-transfer fluid circulating in the jacket of the reactor. The maximum autogenous pressure reaches 31.2 bar (i.e., about 32 bar of absolute pressure).

After a reaction time of one hour under these conditions, the mixture is cooled, with stirring. About 50 minutes are required to reach room temperature.

Analysis of the hydracids and the organic compounds in the reaction mixture gives the following results:

degree of conversion of the 1,1,1-trichloroethane = 92.6% degree of conversion of the $CH_3-CCl_3$
to $CH_3-CF_3 = 0.07\%$
to $CH_3-CF_2Cl = 12.3\%$
to $CH_3-CFCl_2 = 79.2\%$
ratio $CF_3-CH_3/CF_2Cl-CH_3 = 0.6\%$

EXAMPLE 2

Example 1 is repeated but without stirring. The maximum absolute autogenous pressure reaches 31 bar and the following results are obtained:

degree of conversion of the $CH_3-CCl_3=89\%$
degree of conversion of the $CH_3-CCl_3$
  to $CH_3-CF_3=0.13\%$
  to $CH_3-CF_2Cl=14.5\%$
  to $CH_3-CFCl_2=71.7\%$
ratio $CF_3-CH_3/CF_2Cl-CH_3=0.9\%$ This last ratio shows that it is preferable to carry out the reaction with stirring.

EXAMPLE 3

Example 1 is repeated but the molar ratio $HF/CH_3-CCl_3$ is modified from 2.2 to 5 by using the following amounts of reactants:
2.8 g of triflic acid
61.8 g of 1,1,1-trichloroethane
46.3 g of hydrofluoric acid In this experiment, performed under conditions identical to those of Example 1 (stirring at 700 rpm; 100° C.), the maximum absolute autogenous pressure reaches 36 bar. The results obtained are as follows:
degree of conversion of the $CH_3-CCl_3=93.5\%$
degree of conversion of the $CH_3-CCl_3$
  to $CH_3-CF_3=0.4\%$
  to $CH_3-CF_2Cl=37.2\%$
  to $CH_3-CFCl_2=52.6\%$
ratio $CH_3-CF_3/CH_3-CF_2Cl=1.1\%$

COMPARATIVE EXPERIMENT NO. 1

The procedure is the same as for Example 1 except that no catalyst is added. The amounts of reactants used are as follows:
66.8 g of 1,1,1-trichloroethane
21.9 g of hydrofluoric acid The maximum absolute autogenous pressure reaches 27 bar. The following results are obtained:
degree of conversion of the $CH_3-CCl_3=81.2\%$
degree of conversion of the $CH_3-CCl_3$
  to $CH_3-CF_3=0.03\%$
  to $CH_3-CF_2Cl=2.9\%$
  to $CH_3-CFCl_2=78.0\%$
ratio $CH_3-CF_3/CH_3-CF_2Cl=1\%$ Comparison of the results of this experiment with those obtained in Example 1 shows that the catalyst according to the invention makes it possible to improve the selectivity in terms of $CH_3-CF_2Cl$, while the degree of conversion of $CH_3-CCl_3$ to $CH_3-CF_2Cl$ is four times greater.

COMPARATIVE EXPERIMENT NO. 2

This experiment is performed in the presence of $SbCl_5$ as the catalyst and at a temperature of 65° C. with the following reactants, introduced in the order indicated:
6 g of $SbC_5$
66.8 g of $CH_3-CCl_3$
21.9 g of HF The results obtained after one hour and with stirring at 700 rpm (maximum absolute pressure reached: 36 bar) are as follows:
degree of conversion of the $CH_3-CCl_3=98.5\%$
degree of conversion of the $CH_3-CCl_3$
  to $CH_3-CF_3=28.4\%$
  to $CH_3-CF_2Cl=64.4\%$
  to $CH_3-CFCl_2=1.7\%$
ratio $CH_3-CF_3/CH_3-CF_2Cl=44.1\%$ Although carried out at a lower temperature, disfavoring the formation of $CH_3-CF_3$, this experiment clearly shows the influence of the nature of the catalyst on the desired selectivity in terms of $CH_3-CF_2-Cl$.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for the manufacture of 1-chloro-1,1-difluoroethane comprising reacting in the liquid phase hydrofluoric acid with 1,1,1-trichloroethane and/or 1,1-dichloro-1-fluoroethane, with a perfluoroalkanesulphonic acid $CF_3-(CF_2)_n-SO_3H$, n being an integer ranging from 0 to 7, used as a catalyst.

2. The process according to claim 1, wherein the catalyst is triflic acid.

3. The process according to claim 1 wherein 1 to 10 mol of catalyst are used per 100 mol of 1,1,1-trichloroethane.

4. The process according to claim 3, wherein 3 to 5 mol of catalyst are used.

5. The process according to claim 1, wherein the reaction is carried out at a temperature which ranges from 80° to 150° C.

6. The process according to claim 5, wherein the reaction temperature is between 100° and 110° C.

7. The process according to claim 1, wherein the molar ratio $HF/CH_3-CCl_3$ is between 2 and 5.

8. The process according to claim 1, wherein total reaction pressure is between 15 and 50 bar.

9. The process according to claim 1, wherein the process is carried out with stirring.

10. The process according to claim 1, wherein the process is carried out batchwise under autogenous pressure of the reaction mixture.

11. The process according to claim 1, wherein the process is carried out continuously under a pressure between 15 and 20 bar.

12. The process according to claim 1, wherein the 1,1-dichloro-1-fluoroethane formed is recycled.

* * * * *